United States Patent [19]

Korsgaard et al.

[11] Patent Number: 5,696,149
[45] Date of Patent: Dec. 9, 1997

[54] USE OF 3,4-DIPHENYL CHROMANS FOR THE MANUFACTURE OF A PHARMACEUTICAL COMPOSITION FOR THE TREATMENT OR PROPHYLAXIS OF CEREBRAL DEGENERATIVE DISORDERS

[75] Inventors: Niels Korsgaard, Værløse; Michael Shalmi, København; Birgitte Hjort Guldhammer, Hillerød, all of Denmark

[73] Assignee: Novo Nordisk A/S, Bagsvaerd, Denmark

[21] Appl. No.: 585,012

[22] Filed: Jan. 11, 1996

[30] Foreign Application Priority Data

Jan. 20, 1995 [DK] Denmark ................... 0068/95
Jun. 30, 1995 [DK] Denmark ................... 0776/95

[51] Int. Cl.[6] ............... A61K 31/40; A61K 31/35
[52] U.S. Cl. ............................. 514/422; 514/456
[58] Field of Search ........................... 514/456, 422

[56] References Cited

U.S. PATENT DOCUMENTS

| 3,822,287 | 7/1974 | Bolger | 260/326.5 |
|---|---|---|---|
| 4,447,622 | 5/1984 | Salman et al. | 548/525 |
| 5,280,040 | 1/1994 | Labroo et al. | 514/422 |
| 5,451,603 | 9/1995 | Piggott | 514/422 |
| 5,480,903 | 1/1996 | Piggott | 514/422 |

OTHER PUBLICATIONS

Ray et al. "An X-ray Crytallographic Study of the Nonsteroidal Contraceptive Agent Centchroman", J. Med. Chem. Soc., vol. 37, pp. 696-700 (1993) 1994.

Primary Examiner—Raymond Henley, III
Attorney, Agent, or Firm—Steve T. Zelson; Cheryl H. Agris

[57] ABSTRACT

The present invention provides novel uses of compounds of general formula I

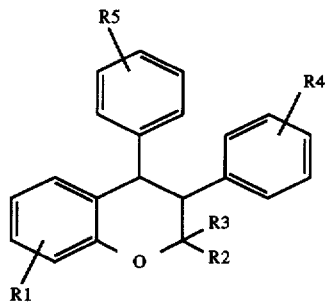

wherein $R^1$, $R^4$ and $R^5$ are individually hydrogen, hydroxy, halogen, trifluoromethyl, lower alkyl, lower alkoxy or (tertiary amino)(lower alkoxy); and $R^2$ and $R^3$ are individually hydrogen or lower alkyl, or as a pharmaceutically acceptable salt thereof in combination with a pharmaceutically acceptable carrier for the manufacture of a pharmaceutical composition for the treatment or prophylaxis of cerebral degenerative disorders.

21 Claims, No Drawings

USE OF 3,4-DIPHENYL CHROMANS FOR THE MANUFACTURE OF A PHARMACEUTICAL COMPOSITION FOR THE TREATMENT OR PROPHYLAXIS OF CEREBRAL DEGENERATIVE DISORDERS

FIELD OF THIS INVENTION

The present invention relates to the use of compounds of the general formula I for the treatment of patients suffering from cerebral degenerative disorders, e.g. Alzheimer's disease, and prophylaxis hereof. The present invention also embraces pharmaceutical compositions comprising these compounds and methods of using the compounds and their pharmaceutical compositions.

BACKGROUND OF THIS INVENTION

In classifying diseases of the nervous system, it is customary to designate a group of them as degenerative, indicating that they are characterized by gradually evolving, relentlessly progressive neuronal death occurring for reasons that are still largely unknown. The identifications of these diseases depends upon exclusion of such possible causative factors as infections, metabolic derangements, and intoxications. A considerable proportion of the disorders classed as degenerative are genetic. Others, however, occur only sporadically as isolated instances in a given family. Classification of the degenerative disorders cannot be based upon any exact knowledge of etiology or pathogenesis; their subdivision into individual syndromes rests on descriptive criteria based largely upon neuropathologic and clinical aspects. Many of the degenerative nervous system diseases progress uninfluenced by therapeutic measures.

Alzheimer's disease (AD) is perhaps the most important of all the degenerative diseases because of its frequent occurrence and devastating nature. AD is a degenerative brain disorder characterized clinically by progressive loss of memory, cognition, reasoning, judgement and emotional stability that gradually leads to profound mental deterioration and ultimatively death. AD is the most common cause of progressive mental failure (dementia) in the elderly and is believed to represent the fourth most common medical cause of death in the United States. The disease is currently estimated to affect about two to three million individuals in the United States alone. To date, many of the degenerative nervous system diseases, including AD, progress uninfluenced by any therapeutic measures.

The outstanding pathologic feature is death and disappearance of nerve cells in the cerebral cortex. This leads ultimatively to extensive convolutional atrophy, especially in the frontal, parietal, and medial temporal regions. Two kinds of microscopic lesions are distinctive for the disease. The first, originally described by Alzheimer, consists of intraneuronal accumulations of filamentous material in the form of loops, coils, or tangled masses referred to as Alzheimer neurofibrillar tangles. Their exact nature is currently under active investigations, but the neuropathologic evidence strongly suggests that these fibrillar masses of amyloidogenic nature are of major importance in bringing about the death of the neurons. The second histopathologic change that characterizes AD is the presence of intracortical clusters of thickened neuronal processes, both axons and dendrites.

Several lines of evidence indicate that progressive cerebral deposition of particular amyloidogenic proteins, β-amyloid proteins (βAP), plays a pivotal role in the pathogenesis of AD and can precede cognitive symptoms by years or decades (Selkoe D J, Neuron 6:487, 1991). Recently, it has been shown that βAP is released from neuronal cells grown in cell culture and is present in cerebrospinal fluid (CSF) of both normal individuals and AD patients (Seubert et al., Nature 359:325, 1992).

Biochemical studies show that choline acetyltransferase, the key enzyme required for the synthesis of acetylcholine, is decreased in the cerebral cortex in AD. The major source of the neocortical cholinergic innervation is a group of neurons situated in the basal part of the forebrain just beneath the corpus striatum, the nucleus basalis of Meynert. This nucleus is a site of major neuronal loss and of frequent Alzheimer neurofibrillar tangles. Thus, impairment of cholinergic transmission may play a part in the clinical expression of the disease. However, attempted therapy with cholinomimetic agents have been largely unsuccessful. In contrast, recent studies have indicated that estrogen influences cholinergic function through a stimulation of choline acetyltransferase (Kaufman H et al., Brain Res 453:389, 1988) and that it also increases the binding sites of hypothalamic nicotinic acetylcholine receptors (Morley B J et al., Brain Res 278:262, 1983). Furthermore, it has been suggested that low dose estrogen replacement therapy may have a beneficial effect on AD (Okura T et al., Menopause 1:125, 1994).

However, the effects of estrogen in rats show sex difference: estradiol administration increased the activity of choline acetyltransferase in nuclei in females that had undergone oophorectomy, but had a decremental or no effect in castrated males (Luine VN & McEwen B S, Neuroendocrinology 36:36:475, 1983). Furthermore, there are significant side effects of estrogen replacement therapy, the most disturbing being the well-established correlation with endometrial and breast cancers. The incidence of carcinoma is both dose- and duration-dependent.

Avoidance of the cancer risk has been achieved by the concomitant use of a progestogen with estrogen. This combination, however, causes menses to return, which many women find unacceptable. A further disadvantage is that the long term effects of the progestogen have not been fully determined.

There remains a need in the art for compositions and methods that are useful in the treatment or prophylaxis of degenerative cerebral disorders including Alzheimer's disease. There is a further need for such compositions that lack the undesirable side effects of estrogen.

Centchroman is a non-steroidal compound known to have antiestrogenic activity. It is in use in India as an oral contraceptive (see, for example, Salman et al., U.S. Pat. No. 4,447,622; Singh et al., Acta Endocrinol. (Copenh)1.26 (1992), 444–450; Grubb, Curr. Opin-.Obstet. Gynecol. 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., Int. J. Cancer 43 (1989), 781–783). Recently, centchroman as a racemate has been found potent as a cholesterol lowering pharmaceutical expressed by a significant decrease of the serum concentrations (S. D. Bain et al., J. Min.Bon.Res. 9 (1994), 394).

U.S. Pat. No. 5,280,040 describes methods and pharmaceutical compositions for reducing bone loss using 3,4-diarylchromans and their pharmaceutically acceptable salts.

One object of the present invention is to provide compounds which can effectively be used in the treatment or prophylaxis of cerebral degenerative disorders, e.g. Alzheimer's disease.

BRIEF DESCRIPTION OF THIS INVENTION

It has, surprisingly, been found that compounds of the general formula I as stated in Claim 1 can be used in the treatment or prophylaxis of cerebral degenerative disorders, e.g. Alzheimer s disease.

DETAILED DESCRIPTION OF THIS INVENTION

The present invention is based in part on the discovery that a representative 3,4-diarylchroman, centchroman (3,4-trans-2,2-dimethyl-3-phenyl-4-[4-(2-(pyrrolidin-1-yl)ethoxy)phenyl]-7-methoxychroman) is effective against cerebral degenerative disorders, e.g. Alzheimer's disease, inter alia in mice or rats e.g. Fisher rats. Centchroman is a racemic mixture. These animal models are generally recognized models of cerebral degeneative disorders, e.g. Alzheimer's disease. These data thus indicate that the 3,4-diarylchromans of formula I are useful as therapeutic and preventive agents against cerebral degenerative disorders, e.g. Alzheimer's disease, in mammals, including primates such as humans.

Within the present invention, compounds of formula I as stated in Claim 1 are administered as drugs against cerebral degenerative disorders, e.g. Alzheimer's disease. Within formula I, $R^1$, $R^4$ and $R^5$ are individually hydrogen, halogen, trifluoromethyl, lower alkyl, lower alkoxy or (tertiary amino)(lower alkoxy); and $R^2$ and $R^3$ are individually hydrogen or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. The tertiary amino radical may be a N,N-dialkylamine such as a N,N-dimethylamino, N,N-diethylamino, N,N-dipropylamino and N,N-dibutylamino or a polymethyleneimine, e.g. piperidine, pyrrolidine, N-methylpiperazine or morpholine. Herein, the term "(tertiary amino)-(lower alkoxy)" is a lower alkoxy group which is substituted by a tertiary amino group. Preferred compounds include those in which $R^1$ is lower alkoxy; $R^2$ and $R^3$ are lower alkyl, especially methyl; $R^4$ is hydrogen; and $R^5$ is (tertiary amino)(lower alkoxy) of the polymethyleneimine type. Within particularly preferred embodiments, $R^1$ is in the 7-position and is lower alkoxy, particularly methoxy; each of $R^2$ and $R^3$ is methyl, $R^4$ is hydrogen, and $R^5$ is in the 4-position and is a (tertiary amino)-(lower alkoxy) radical such as 2-(pyrrolidin-1-yl)ethoxy. To be included by this invention are all pharmaceutically acceptable salts of the mentioned compounds of formula I.

It is preferred to use the compounds of formula I in the transconfiguration. These compounds may be used as racetalc mixtures, or the isolated stereoisomers, e.g. d- or l-enantiomers, may be used. The trans-l-enantiomers are more preferred.

A particularly preferred compound for use within the present invention is centchroman consisting of l-centchroman and d-centchroman. Probably, l-centchroman has the formula IV

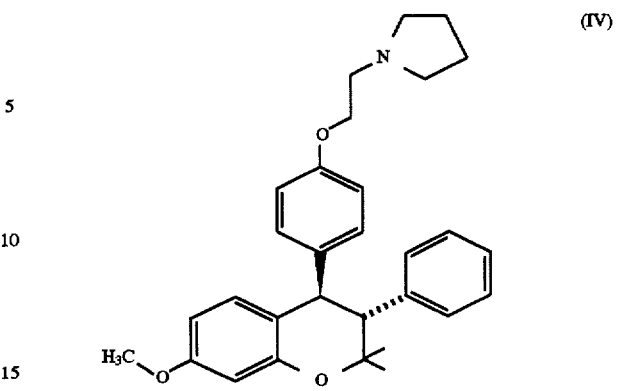

3,4-diarylchromans are prepared according to known methods, such as those disclosed in U.S. Pat. No. 3,340,276 to Carney et al., U.S. Pat. No. 3,822,287 to Bolger, and Ray et al., J. Med.Chem. 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. If $R^2$ is different from $R^3$ and $R^4$ is different from $R^5$, the general formula I covers 8 optical isomers.

Within the present invention, 3,4-diarylchromans of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4-diarylchromans of formula I and their salts are useful within human and veterinary medicine, for example, in the treatment or prophylaxis of patients suffering from cerebral degenerative disorders, e.g. Alzheimer's disease. For use within the present invention, 3,4-diarylchromans of formula I and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in Remington's Pharmaceutical Sciences, Gennaro, ed., Mack Publishing Co., Easton, Pa., 1990.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered one or more times per day or week. An effective amount of such a pharmaceutical composition is the amount that provides a clinically significant effect against cerebral degenerative disorders, e.g. Alzheimer's disease. Such amounts will depend, in part, on the particular condition to be treated, age, weight, and general health of the patient, and other factors evident to those skilled in the art.

The pharmaceutical compositions containing a compound of formula I may be administered in unit dosage form one or more times per day or week. In the alternative, they may be provided as controlled release formulations suitable for derreal implantation. Implants are formulated to provide release of active compound over the desired period of time, which can be up to several years. Controlled-release formulations are disclosed by, for example, Sanders et al., *J. Pharm. Sci.* 73 (1964), 1294–1297, 1984; U.S. Pat. No. 4,489,056; and U.S. Pat. No. 4,210,644, which are incorporated herein by reference.

Examples of preferred compounds of formula I are centchroman as a racemic mixture and as I-centchroman and d-centchroman. Furthermore, 3,4-trans-2, 2-dimethyl-3-phenyl-4-[4-(2-(pyrrolidin- 1-yl)ethoxy) phenyl]-7-hydroxychroman is a preferred compound. The more preferred compound is 1,3,4-trans-2,2-dimethyl-3-phenyl-4-[4-(2(pyrrolidin-1-yl)-ethoxy)phenyl]-7-methoxychroman.

The present invention is further illustrated by the following examples which, however, are not to be construed as limiting the scope of protection.

The features disclosed in the foregoing description and in the following examples may, both separately and in any combination thereof, be material for realising the invention in diverse forms thereof.

EXAMPLES

Test 1

Transgenic mice overexpressing the V717F β-amyloid precursor protein are purchased from Athena Neurosciences, Inc. San Francisco, Calif., USA. Only heterozygous animals are used. Histopathologic examination of the brains from these animals exhibits deposits of human amyloid β-peptide (Aβ) in the hippocampus, corpus callosum and cerebral cortex after 6–9 months. The accumulation of peptide increase with age and after 9 months the pattern resembles that seen in Alzheimer's disease.

Between 10 and 50 transgenic mice are used for the study. The animals are housed in metal hanging cages in groups of two and have ad libitum access to food and water for one week. Room temperature is maintained at 20°±1.5° C. with a minimum relative humidity of 40%. The photoperiod in the room is 12 hours light and 12 hours dark.

After a one week of acclamation period the animals are at random divided into five treatment groups of between 2 and 10 animals and daily oral treatment with the test compound is initiated. The test compound is given in four different doses between 0 and 75 mg/kg/day for one month. Following the dosing period the animals are weighed and sacrificed by asphyxiation with $CO_2$. The brain is removed, weighed and immediately frozen in cooled isopentane. The brains are serially sectioned on a cryostat (10–50 μm thick sections) and mounted on marked and poly-L-lysine coated glass slides.

Mouse brain sections are labelled with antiserum R1280 generated against synthetic human Aβ 1–40 peptide. Peroxidase standard rabbit IgG kit (Vector Labs) is used as recommended, with 3,3'-diaminobenzidine (DAB) as the chromogen. Positive plaques are counted and measured quantitatively using stereological techniques. Activity is indicated by a decrease in size and number of plaques size in the brain.

Test 2

Five to fifty women are selected for the clinical study. The women are postmenopausal, i.e. having ceased menstruating for between 6 and 12 month prior to the sturdys' initiation, have been diagnosed with early stage Alzheimer's disease (AD), are expected to have worsening symptoms of AD within the study period, but are in good general health otherwise. The study has a placebo control group, i.e. the women are divided into two groups, one of which receives the active agent of this invention and the other receives the placebo. The patients are bench-marked as to memory, cognition, reasoning and other symptoms associated with AD. Women in the test group receive between 1–1000 mg of the active agent per day by the oral route. They continue this therapy for 6–36 months. Accurate records are kept as to the benchmarked symptoms in both groups and at the end of the study these result are compared. The results are compared both between members of each group and also the results for each patient are compared to the symptoms for each patient before the study began. Activity of the test result is illustrated by an inhibition of any one or more of the symptoms of AD in the patients taking the test drug.

We claim:

1. A method for treatment of cerebral degenerative disorders comprising administering to a patient in need of such treatment a compound of formula I

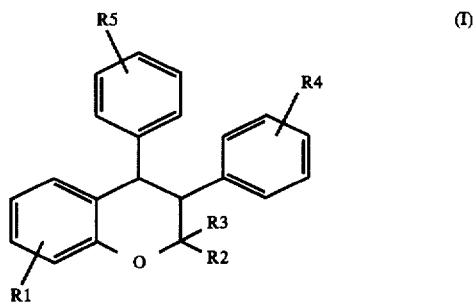

(I)

wherein R1, R4, and R5 are individually hydrogen, hydroxy, halogen, trifluoromethyl, lower alkyl, lower alkoxy or (tertiary amino) (lower alkoxy); and R2 and R3 are individually hydrogen or lower alkyl, or a pharmaceutically acceptable salt thereof in an amount sufficient to treat said disorders.

2. The method according to claim 1 in which said patient has Alzheimer's Disease.

3. The method according to claim 1 in which R1 is lower alkoxy.

4. The method according to claim 1 wherein R1 is methoxy.

5. The method according to claim 1 wherein R2 is lower alkyl.

6. The method according to claim 1 wherein R2 is methyl.

7. The method according to claim 1 wherein R3 is lower alkyl.

8. The method according to claim 1 wherein R3 is methyl.

9. The method according to claim 1 wherein R4 is hydrogen.

10. The method according to claim 1 wherein R5 is tertiary amino lower alkoxy.

11. The method according to claim 1 wherein R5 is 2-(pyrrolidin-1-yl)ethoxy.

12. The method according to claim 1 wherein said compound has the formula III:

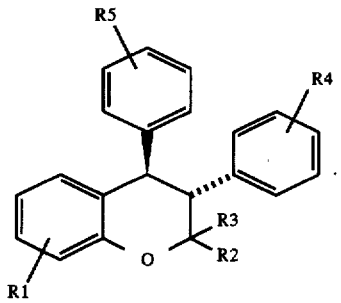

(III)

13. The method according to claim 12 wherein said compound is an isolated d- or l-enantiomer.

14. The method according to claim 13 wherein said compound is an isolated l-enantiomer.

15. The method according to claim 1 wherein said compound is 3,4-trans-2,2-dimethyl-3-phenyl-4-[4-(2-(pyrrolidin-1-yl)ethoxy)phenyl]-7-methoxychroman.

16. The method according to claim 1 wherein said compound is an isolated d- or l-enantiomer of 3,4-trans-2,2-dimethyl-3-phenyl-4-[4-(2-(pyrrolidin-1-yl) ethoxy)phenyl]-7-methoxychroman.

17. The method according to claim 1 wherein said compound is 1-3,4-trans-2,2-dimethyl-3-phenyl-4-[4-(2-(pyrrolidin-1-yl)ethoxy)phenyl]-7-methoxychroman.

18. The method according to claim 1 wherein said compound is administered orally.

19. The method according to claim 1 wherein said compound is administered in a range from about 0.001 to 75 mg/kg patient per day.

20. The method according to claim 1 wherein said compound is administered in the form of a dermat implant.

21. A method for reducing size and number of plaques in a patient's brain comprising administering to a patient in need of such treatment a compound of formula I

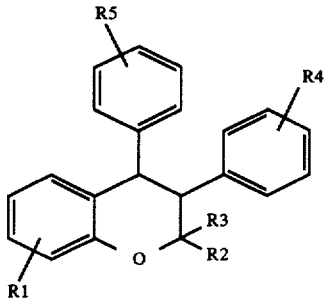

(I)

wherein R1, R4, and R5 are individually hydrogen, hydroxy, halogen, trifluoromethyl, lower alkyl, lower alkoxy or (tertiary amino) (lower alkoxy); and R2 and R3 are individually hydrogen or lower alkyl, or a pharmaceutically acceptable salt thereof in an amount sufficient to reduce the size and number of plaques in a patient's brain.

* * * * *